US006106774A

United States Patent [19]

Monticello et al.

[11] Patent Number: 6,106,774

[45] **Date of Patent: *Aug. 22, 2000**

[54] READY TO USE AQUEOUS HARD SURFACE CLEANING AND DISINFECTING COMPOSITIONS CONTAINING HYDROGEN PEROXIDE

[75] Inventors: Michael Vincent Monticello, Saddle Brook; George Robert Mayerhauser, Ringwood, both of N.J.

[73] Assignee: Reckitt Benckiser Inc., Wayne, N.J.

[ * ] Notice: This patent is subject to a terminal disclaimer.

[21] Appl. No.: 09/227,464

[22] Filed: Jan. 8, 1999

Related U.S. Application Data

[63] Continuation-in-part of application No. 08/928,097, Sep. 12, 1997, Pat. No. 5,891,392.

[30] Foreign Application Priority Data

Nov. 12, 1996 [GB] United Kingdom .................. 9623473

[51] Int. Cl.[7] .......................... A01N 39/00; A61K 33/40

[52] U.S. Cl. .......................... 422/28; 252/186.43; 422/1; 424/616; 510/375; 510/421

[58] Field of Search .................. 422/1, 28; 252/186.43; 510/367, 370, 375, 405, 421, 437; 424/616

[56] References Cited

U.S. PATENT DOCUMENTS

| | | | |
|---|---|---|---|
| H1265 | 12/1993 | Brady et al. | 514/665 |
| 4,040,977 | 8/1977 | Eggensperger et al. | 422/36 |
| 5,145,663 | 9/1992 | Simmons | 422/28 |
| 5,271,860 | 12/1993 | Schwadtke et al. | 252/96 |
| 5,405,602 | 4/1995 | Simmons et al. | 424/47 |
| 5,441,723 | 8/1995 | Simmons | 424/47 |
| 5,637,306 | 6/1997 | Simmons et al. | 424/405 |

*Primary Examiner*—Krisanne Thornton
*Attorney, Agent, or Firm*—Fish & Richardson P.C.

[57] ABSTRACT

Disclosed are ready to use aqueous cleaning and disinfecting composition which includes the following constituents by weight:

0.1–20%wt. of a $C_1$–$C_6$ monohydric alcohol;

1.0–10%wt. of a glycol ether, or butoxypropanol or propoxypropanol;

0.1–12%wt. of a detersive surfactant particularly those selected from anionic, cationic, nonionic and amphoteric surfactants;

0.1–10%wt. of hydrogen peroxide;

0.1–7%wt. of an acid;

to 100%wt. water;

wherein the said composition is at an acidic pH. The composition may include minor amounts of further conventional additives.

Methods of cleaning and disinfecting surfaces are also disclosed.

21 Claims, No Drawings

READY TO USE AQUEOUS HARD SURFACE CLEANING AND DISINFECTING COMPOSITIONS CONTAINING HYDROGEN PEROXIDE

CROSS-REFERENCE TO RELATED APPLICATIONS

This application is a continuation in part of U.S. Ser. No. 08/928,097, filed Sep. 12, 1997 now U.S. Pat. No. 5,891, 392.

FIELD OF THE INVENTION

The present invention is directed to aqueous, ready to use cleaning and disinfectant compositions which include hydrogen peroxide as an active disinfecting constituent, as well as methods for their production and methods for cleaning and disinfecting surfaces which include such compositions.

The present invention is also directed to a process for the disinfection of hard surfaces.

BACKGROUND ART

Known to the art are various ready to use cleaning and disinfecting compositions which include as germicidal active constituents one or more component such as alcohols, phenolic containing materials, quaternary ammonium compounds as well as acids. However, many such known prior art compositions also frequently induce ocular and/or dermal irritation and this hampers their acceptance and use.

Known from U.S. Pat. No. 5,348,556 are certain specific aqueous compositions which include significant levels of hydrogen peroxide as a disinfecting active constituent, an ammoniated constituent and an alcohol constituent for providing a primary cleaning benefit to a carpet surface.

Known from U.S. Pat. No. 4,518,585 and from U.S. Pat. No. 5,376,387 are certain specific aqueous compositions which include hydrogen peroxide as a disinfecting active constituent which compositions are cited to be useful for the disinfection of hard surfaces; the compositions include an organic triazole corrosion inhibitor.

The current state of the art indicates the need for improved disinfecting compositions, particularly in a ready to use form, which may be classed as broad spectrum disinfecting compositions, but preferably may be classed as hospital strength disinfecting compositions. This is particularly true for organisms which are know to those skilled in the art as more difficult to kill than *Staphylococcus aureus* (gram-positive type pathogenic bacteria) (ATCC 6538), *Salmonella choleraesuis* (gram-negative type pathogenic bacteria) (ATCC 10708), and *Pseudomonas aeruginosa* (ATCC 15442) which are commonly used as test organisms in evaluating sanitization or disinfection efficacy of a composition. As is known, many diseases are associated with the presence of such further organisms (described below) which are commonly understood by those skilled in the art as being more resistant to eradication than *Staphylococcus aureus, Salmonella choleraesuis* and *Pseudomonas aeruginosa.*

The current state of the art also indicates the need for improved methods for the disinfection, and preferably the combined disinfection and cleaning of hard surfaces. It is to these needs, as well as others, that the present invention is directed.

SUMMARY OF THE INVENTION

According to one aspect of the present invention there is provided a ready to use aqueous cleaning and disinfecting composition which includes the following constituents by weight:

- 0.1–20%wt. of a $C_1$–$C_6$ monohydric alcohol;
- 1.0–10%wt. of a glycol ether, or butoxypropanol or propoxypropanol;
- 0.1–12%wt. of a detersive surfactant particularly those selected from anionic, cationic, nonionic and amphoteric surfactants;
- 0.1–10%wt. of hydrogen peroxide;
- 0.1–7%wt. of an acid;
- to 100%wt. water;

wherein the said composition is at an acidic pH, desirably at a pH of from 1 to about 4, and more desirably about 3.5, and may include minor amounts, i.e, to about 2.5%wt. of one or more optional constituents such as fragrances, coloring agents, thickening agents, gelling agents, pH buffers, pH adjusting agents, etc., known to those in the art as useful adjuvants in aqueous cleaning and disinfecting compositions. In most preferred embodiments, the inventive compositions provide hospital strength disinfecting to hard surfaces treated with the compositions.

According to a second aspect of the invention there is provided a ready to use aqueous cleaning and disinfecting composition as described above which is effective in the eradication of, or in providing a reduction in the amount of gram positive or gram negative organisms such as *Staphylococcus aureus, Salmonella choleraesuis* and *Pseudomonas aeruginosa.*

According to a further aspect of the invention there is provided an improved process for providing cleaning and disinfection to a hard surface in need of such treatment which includes the step of providing an effective amount of the aqueous cleaning and disinfecting compositions described herein to said hard surface requiring cleaning and/or disinfecting treatment. According to a preferred embodiment, the improved process utilizes the ready to use aqueous cleaning and disinfecting composition outlined above.

DETAILED DESCRIPTION

The compositions of the invention are acidic, ready to use aqueous cleaning and disinfecting compositions which provide both a good cleaning benefit as well as excellent disinfecting characteristics particularly to hard surfaces. In particularly preferred embodiments the disinfectant characteristics of the compositions are sufficient such that they may be classified as "hospital strength" disinfectant compositions, as they demonstrate excellent antimicrobial activity against both gram positive type bacteria such as exemplified by *Staphylococcus aureus*, and gram negative type bacteria as exemplified by *Salmonella choleraesuis*. Thus the characteristics of both good cleaning and good disinfecting are provided in an aqueous cleaning composition having low amounts of volatile organic materials. These "low VOC" type materials are believed to be attributable to the synergistic effect of the selected constituents and in their relative proportions as taught herein. Compositions having such constituents, which provide the effects described herein are not believed to have been hithero known to the art.

The compositions according to the instant invention include 0.1–20%wt. of a $C_1$–$C_6$ monohydric alcohol. Mixtures of two or more such $C_1$–$C_6$monohydric alcohols may also be used. Exemplary and preferred monohydric alcohols include methanol, ethanol, propanol, isopropanol and n-propanol of which ethanol is most preferred. Such materials are widely commercially available. Desirably, the a $C_1$–$C_6$ monohydric alcohol constituent is present from about 1 to about 12%wt., and yet more desirably from about 3 to about 7%wt.; most desirably about 5%wt. of the $C_1$–$C_6$ monohydric alcohol constituent is present. These low amounts of monohydric alcohol(s) as described herein are preferred so to provide an overall reduction in the amount of volatile organic materials in the inventive compositions. Yet surprisingly, the inventive compositions provide excellent disinfecting properties.

The compositions according to the invention include one or more glycol ethers which form 1.0–10%wt. of the inventive compositions and which provide a desirable stain and soil solublizing effect.

Preferred as solvents in this invention are the glycol ethers having the general structure $R_a$—O—$R_b$—OH, wherein $R_a$ is an alkoxy of 1 to 20 carbon atoms, or aryloxy of at least 6 carbon atoms, and $R_b$ is an ether condensate of propylene glycol and/or ethylene glycol having from 1 to 10 glycol monomer units. Examples of preferred glycol ethers include ethylene glycol monobutyl ether (commercially available as Butyl Cellosolve®), diethylene glycol monobutyl ether (commercially available as Butyl Carbitol®, Union Carbide, Danbury Conn.), as well as butoxypropanol, propoxypropanol, mono-, di- and tri-propylene glycol butyl ethers, and mixtures thereof. These glycol ethers are widely commercially available, for example within the Dowanol™ glycol ether series from The Dow Chemical Company, (Midland, Mich.) or in the Carbitol® and Cellosolve® series from Union Carbide Co. (Danbury, Conn.).

Desirably, the glycol ether solvent is preferably employed in an amount ranging from about 3 to about 7%wt, but more desirably is present in an amount of about 5%wt. based on the total weight of the composition. The glycol ether solvents present in the recited preferred and more preferred amounts have been found to provide a good cleaning benefit, but are not present in excessive amounts which may reduce the overall stability of the cleaning and disinfecting compositions being taught herein.

The compositions according to the invention include 0.1–12%wt. of a detersive surfactant particularly those selected from anionic, cationic, nonionic and amphoteric surfactants. These include known art surfactants.

Useful anionic surfactants include, by way of non-limiting example These include but are not limited to: alkali metal salts, ammonium salts, amine salts, aminoalcohol salts or the magnesium salts of one or more of the following compounds: alkyl sulfates, alkyl ether sulfates, alkylamidoether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkyl sulfoacetates, alkyl phosphates, alkyl ether phosphates, acyl sarconsinates, acyl isethionates, and N-acyl taurates. Generally, the alkyl or acyl radical in these various compounds comprise a carbon chain containing 12 to 20 carbon atoms.

Further exemplary anionic surface active agents which may be used include fatty acid salts, including salts of oleic, ricinoleic, palmitic, and stearic acids; copra oils or hydrogenated copra oil acid, and acyl lactylates whose acyl radical contains 8 to 20 carbon atoms.

More specific examples of suitable alkyl aromatic sulfonate detergents include the straight chain linear alkyl benzene sulfonates wherein the alkyl group contains 10 to 18 carbon atoms, e.g., averaging about 10 to 15, specific examples of which are sodium dodecyl benzene sulfonate, sodium tridecyl benzene sulfonate and sodium higher alkyl benzene sulfonate wherein the alkyl is of 10 to 15 carbon atoms, averaging about 12.5 carbon atoms per molecular proportion.

Other suitable agents are the surface-active sulfated or sulfonated aliphatic compounds, preferably of 12 to 22 carbon atoms. Within the scope of such definition are the sulfuric acid esters of polyhydric alcohols incompletely esterified with higher fatty acids, e.g., coconut oil monoglyceride monosulfate, tallow diglyceride monosulfate; the long chain pure or mixed alkyl sulfates, e.g., lauryl sulfate, cetyl sulfate; the hydroxysulfonated higher fatty acid esters, such as the higher fatty acid esters of low molecular weight alkyl sulfonic acids, e.g., fatty acid esters of isethionic acid; the fatty acid ethanolamide sulfates; the fatty acid amides of aminoalkyl sulfonic acids, e.g., the lauric acid amide of taurine; olefin and paraffin sulfonates; and the like. More particularly, it is preferred to use the sulfated aliphatic compounds containing at least about 8 carbon atoms, especially those having about 12 to about 18 or 22 carbon atoms in the molecule.

Other anionic surface active agents not particularly enumerated here may also find use in conjunction with the compounds of the present invention.

Useful cationic surfactants include, by way of non-limiting example, quaternary ammonium compounds and salts thereof which specifically include quaternary ammonium germicides which may be characterized by the general structural formula:

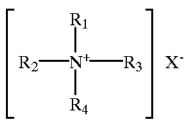

where at least one of $R_1$, $R_2$, $R_3$ and $R_4$ is a hydrophobic, aliphatic, aryl aliphatic or aliphatic aryl radical of from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming anionic radical.

Useful amphoteric surfactants include, by way of non-limiting example include, one or more further known art surfactant compositions, including betaines, ethylene oxide condensates, and fatty acid amides. Further useful amphoteric surfactants include the salts of higher alkyl beta-amino propionic acids, e.g., sodium N-lauryl beta-alanine; the higher alkyl substituted betaines, such as lauryl dimethylammonium acetic acid; as well as amphoteric surfactants of the the imidazoline type exemplified by the disodium salt of 1-(2-hydroxyethyl)-1-(carboxymethyl)-2-(hendecyl)-4,5-dihydroimidazolinium hydroxide.

Exemplary useful betaine surfactants include those according to the general formula $$R—\overset{(+)}{N}(R_1)_2—R_2\overset{(-)}{COO}$$

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R_1$ is an alkyl group containing from 1 to about 3 carbon atoms; and $R_2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Useful fatty acid amides include those which are known to the art. Particular exemplary fatty acid amide surfactants include ammonia, monoethanol, and diethanol amides of fatty acids having an acyl moiety which contains from about 8 to about 18 carbon atoms, and which may be represented in accordance with the formula:

$$R_1—CO—N(H)_{m-1}(R_2OH)_{3-m}$$

where $R_1$ represents a saturated or unsaturated aliphatic hydrocarbon radical of from about 7 to 21 carbon atoms, but preferably from about 11 to 17 carbon atoms; $R_2$ represents a $—CH_2—$ or $—CH_2CH_2—$, and m is an integer from 1 to 3, but is preferably 1. Preferably, $R_1$ is a saturated or unsaturated aliphatic hydrocarbon radical comprising from about 11 to 17 carbon atoms, and m is 1.

Further examples of such compounds include monoethanol amine coconut fatty acid amide and diethanol amine dodecyl fatty acid amide. An exemplary useful fatty acid amide includes cocomonoethanol amide or cocodiethanolamide, which are presently commercially available as MONAMID CMA (Mona Industries, Paterson N.J. (USA)).

An exemplary and preferred amphoteric surfactant is lauramidopropionic acid, which is commercially available in the DERIPHAT series (ex Henkel) or MACKAM series (ex McIntyre Group Inc.) of amphoteric surfactants.

Useful nonionic surfactants which may be included in the concentrate compositions include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethenoxy hydrophobic and hydrophilic elements may vary. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

To be mentioned as particularly useful nonionic surfactants are alkoxylated linear primary and secondary alcohols including those commercially available as PolyTergent® SL series (Olin Chemical Co., Stamford Conn.), Neodol® series (Shell Chemical Co., Houston Tex.); as well as alkoxylated alkyl phenols including those commercially available under the tradename Triton® X series (Union Carbide Chem. Co., Danbury Conn.).

Particularly useful and preferred nonionic surfactants include alcohol alkoxylates, particularly alcohol ethoxylates based linear primary alcohols and linear secondary alcohols. These are preferred as they exhibit excellent compatibility with the other constituents which make up the invention, provide a good soil and stain releasing benefit, are relatively non-toxic to humans, and are not particularly irritating to the skin, eyes or mucosal tissues.

Desirably, the preferred alcohol ethoxylates comprise a system of at least two linear alcohol ethoxylates having different degrees of ethoxylation. More desirably, the linear alcohol ethoxylate having the higher degree of ethoxylation is present in at least an amount equal to the linear alcohol ethoxylate having the lower degree of ethoxylation on a weight basis. Even more desirably, these are present in amounts where the one or more linear alcohol ethoxylate(s) having the higher degree of ethoxylation: the one or more linear alcohol ethoxylate(s) having the lower degree of ethoxylation are present in the ratio of from 1:1 to 4:1 on a weight basis. One exemplary system of two nonionic surfactants is Neodol® 23-6.5, a nonionic alcohol $C_9$–$C_{11}$ethoxylate and having an average of 6.5 mols of ethoxylation per mol of the alcohol, and Neodol® 91-8, a nonionic alcohol $C_9$–$C_{11}$ethoxylate and having an average of 8 mols of ethoxylation per mol of the alcohol. In this exemplary system, the Neodol® 23-6.5 is present in an amount of from 1.5%wt. to 4.0%wt., and the Neodol® 91-8 is present in an amount of from 3.0%wt. to 6.0%wt. but more desirably the amount of Neodol®) 91-8 equals or exceeds the amount of Neodol® 23-6.5 present.

The detersive surfactants may be a single surfactant or may be a mixture of two or more surfactants. The total amount of the detersive surfactants present in the inventive compositions comprise up to 12%wt. based on the total weight of the composition. Desirably, the one or more detersive surfactant comprises between about 0.1%wt. to about 12%wt., more desirably between about 3%wt. to about 10%wt., and especially preferably the amounts exemplified in the Examples. Particularly preferred detersive surfactants are described in the Examples, below. In certain particularly preferred embodiments, the compositions do not include a nonionic surfactant.

The ready to use cleaning and disinfecting compositions of the invention also include hydrogen peroxide as a primary disinfecting constituent. The hydrogen peroxide is present in no more than about 10%wt. based on the total weight of the ready to use aqueous cleaning and disinfecting composition but is desirably less, i.e., is present in an amount of from about 0.01%wt. to about 5%wt., yet more desirably about 0.05%wt. to about 1.55%wt. A minimum of 1.0%wt. $H_2O_2$ is required to achieve hospital strength level disinfection although it is believed lower levels of disinfection against a narrower range of microorganisms may be attained with lesser amounts of hydrogen peroxide than the preferred minimum amount of 1%wt. Desirably, the hydrogen peroxide is provided in an amount of 1.5%wt. This amount is preferred in order to allow for a slight loss of $H_2O_2$ during the shelf life of the ready to use cleaning and disinfecting composition. Higher concentrations of $H_2O_2$ may be provided. However they are to be avoided, as it has been observed that such higher levels will cause an increase in skin whitening and is therefore not desirable.

According to certain preferred embodiments of the invention, they hydrogen peroxide present is in excess of 1.5%wt.

An acid is present in the inventive compositions. The acid may be an inorganic acid or may be an organic acid including organic compounds comprising one or more carboxylic groups. Mixtures of acids are also contemplated as being useful. These one or more acids present provide the desired acidic characteristic to the compositions. Such an acid is present in effective amounts to establish a targeted pH range for compositions according to the invention. While any of a number of acids may be used, particularly preferred acids include those described amongst the Examples. Generally, the acid may be present in amounts of up to about 7%wt. of the total composition, but more desirably, it is present in an amount to comprise from about 1.0% to about 5%. According to certain particularly preferred embodiments the acid is a single acid. According to especially preferred embodiments the acid is selected from: citric, tartaric, sulfamic, malic, glutaric, glycolic and phosphoric acids.

The cleaning and disinfecting compositions of the invention are adjusted to an acidic pH, generally less than 7, but desirably are maintained at an acidic pH of about 1 to about 4 and less, and more desirably to about 3.5. Such may be achieved primarily by the addition of effective amounts of the one or more inorganic acids and/or organic acids, as denoted above. Such pH may also be maintained, for example, by the inclusion of one or more pH buffers as described with reference to the optional constituents.

As the inventive compositions are aqueous in nature, water is a major constituent. Desirably deionized water is used. Water is added in a sufficient amount, or "quantum sufficient" to provide 100%wt. of the compositions.

The constituents described herein are known to the art, and are commercially available from various sources including those described in *McCutcheon 's Emulsifiers and Detergents* (Vol. 1), *McCutcheon 's Functional Materials* (Vol. 2), North American Edition, 1991; Kirk-Othmer, *Encyclopedia of Chemical Technology,* 3rd Ed., Vol. 22, the contents of which are herein incorporated by reference For any particular composition, such optional ingredients should be compatible with the other ingredients present.

The compositions of the invention may include minor amounts of one or more optional constituents, as described hereinafter.

Foaming agents, and foam stabilizing agents may be provided. As is known to the art, such may be commercially desirable in compositions according to the invention. Such may be especially desirable where the composition is packaged in a pressurized device, i.e., an aerosol canister or in a hand-held pumpable container (such as a hand-held trigger spraying vessel), so that upon the application of the composition to the stain a foaming action is observed by the consumer when dispensed onto a surface. Known foaming agents may be used including the following exemplary compositions: alkyl sulfates, alkyl sulfonates, amine oxides, alkanolamides, as well as others known to the art.

Further optional, but desirable constituents include fragrances, natural or synthetically produced. Such fragrances may be added in any conventional manner, admixing to a composition or blending with other constituents to form a composition, in amounts which are useful to enhance or impart the desired scent characteristics to the composition.

In compositions which include a fragrance, it is frequently desirable to include a fragrance solubilizer which assists in the dispersion, solution or mixing of the fragrance constituent in an aqueous base. These include known art compounds, such as condensates of 2 to 30 moles of ethylene oxide with sorbitan mono- and tri-$C_{10}$–$C_{20}$ alkanoic acid esters which are also known as nonionic surfactants. Further examples of such suitable surfactants include water soluble nonionic surfactants of which many are commercially known and by way of non-limiting example include the primary aliphatic alcohol ethoxylates, secondary aliphatic alcohol ethoxylates, alkylphenol ethoxylates and ethylene-oxide-propylene oxide condensates on primary alkanols, and condensates of ethylene oxide with sorbitan fatty acid esters. This fragrance solubilizer component is added in minor amounts, so as to be effective in aiding in the solubilization of the fragrance component, but not in any significantly greater proportion, such that it would be considered as a detergent constituent. Such minor amounts recited herein are generally up to about 0.3% by weight of the total composition but is more generally an amount of about 0.1% by weight and less, and preferably is present in amounts of about 0.05% by weight and less.

Further optional, but advantageously included constituents are one or more coloring agents which find use in modifying the appearance of the compositions and enhance their appearance from the perspective of a consumer or other end user. Known coloring agents may be incorporated in the compositions in any effective amount to improve or impart to compositions a desired appearance or color. Such coloring agents may be added in a conventional fashion, i.e., admixing to a composition or blending with other constituents used to form a composition.

The use of one or more known pH adjusting agents, including agents known to the art such as mineral acids, basic compositions, and organic acids may be used in minor amounts. An exemplary composition includes citric acid, such as is available in an anhydrous salt form of an alkali metal citric acid. The addition of an effective amount of a pH adjusting agent is useful in establishing a targeted pH range for compositions according to the invention.

An effective amount of a pH buffering composition so to maintain the pH of the inventive compositions may also be added. While the composition of the invention generally does not require a pH buffering composition, its use may provide the benefit of hard water ion sequestration, should the inventive composition be diluted with further water by the consumer or other end user. Any pH buffering compound or pH buffer composition which is compatible with the aqueous compositions taught herein may be used, and many of these are well known to the art. Examples of such useful pH buffer compounds and/or pH buffering systems or compositions include the alkali metal phosphates, polyphospates, pyrophosphates, triphosphates, tetraphosphates, silicates, metasilicates, polysilicates, carbonates, hydroxides, and mixtures thereof. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. Such buffers keep the pH ranges of the compositions of the present invention within acceptable limits. Others, not particularly elucidated here may also be used. Preferably, citric acid, such as is available in an anhydrous salt form of an alkali metal citric acid is added as it is readily commercially available, and effective. The addition of a buffering agent is desirable in certain cases wherein long term, i.e., prolonged storage, is to be anticipated for a composition, as well as ensuring the safe handling of said aqueous composition.

Further useful constituents which may be included are one or more thickening and/or gelling agents which may be added to the hard surface cleaning compositions according to the present invention in order to modify the viscous and/or thixotropic properties thereof. For example, in certain applications it is contemplated that it may be desirable to provide compositions which are more viscous than water, whether for aesthetic or functional reasons. For example, the addition of a suitable amount of a gelling agent may be desired not only for aesthetic reasons but also to limit the spreading of the composition as it is applied to a surface. This function is desirable in providing a means to apply the composition over a limited area, such as directly onto a stain, without applying an excess onto the surrounding area of a surface. This function also aids in the surface retention time on non-horizontal surface, ensuring that the cleaning composition is in contact with a stained surface without flowing off too rapidly. Similarly, thixotropic properties may also be desired under certain circumstances. In order to provide such functional features to the composition, known thickening and gelling agents including, but not limited to, cellulose compounds, xanthan gums, polymers and/or clays may be added.

As denoted above, the aqueous cleaning and disinfecting compositions according to the invention may include minor amounts of one or more optional additives including those known to the art as useful in such compositions. These optional constituents, if present, desirably comprise not more than a total of about 2.5%wt. based on the total weight of the inventive compositions and more desirably are present in lesser amounts.

Aqueous cleaning and disinfecting compositions according to the invention is desirably provided as a ready to use product which may be directly applied to a hard surface. By way of example, hard surfaces suitable include surfaces composed of refractory materials such as: glazed and unglazed tile, brick, porcelain, ceramics as well as stone including marble, granite, and other stones surfaces; glass; metals; plastics e.g. polyester, vinyl; fiberglass, and other hard surfaces known to the industry. Hard surfaces which are to be particularly denoted are lavatory fixtures such as shower stalls, bathtubs and bathing appliances (racks, curtains, shower doors, shower bars) toilets, bidets, wall and flooring surfaces especially those which include refractory materials and the like. Further hard surfaces which are to be denoted are those associated with kitchen environments and other environments associated with food preparation, including cabinets and countertop surfaces as well as walls and floor surfaces especially those which include refractory materials, as well as plastics, Formica®, Corian® and stone. Hard surfaces which are to be most particularly denoted include hard surfaces associated with hospital environments, medical laboratories and medical treatment environments. These include hard surfaces found for example in operating theatres, surgical areas and surgical preparation areas as well as surgical recovery areas, surfaces found on moveable equipment, i.e., gurneys, moveable equipment such as instruments, and moveable stands, moveable beds, wheelchairs, and the like, as well as surfaces found of equipment which is not normally moved including operating and examining tables, instruments such as non-moveable monitoring equipment, anaesthesia dispensing equipment, beds and the like. Such hard surfaces described above are to be understood as being recited by way of illustration and not be way of limitation.

The composition is particularly useful for disinfecting and sterilizing surfaces, both animate and inanimate, contaminated with bacterial, fungal and viral microorganisms and/or microbial spores in medical and non-medical situations. The composition offers an excellent alternative to known methods of cleaning surfaces of human and veterinary medicine and surgery and dentistry instruments and objects. Such objects may be treated with the composition at room or elevated temperatures. Also appropriate uses of the composition include industrial and domestic environments because of the excellent disinfecting capabilities of the composition.

The compositions according to the invention are useful in the cleaning and/or disinfecting of surfaces, especially hard surfaces, having deposited soil thereon. In such a process, cleaning and disinfection of such surfaces comprises the step of applying a stain releasing and disinfecting effective amount of a composition as taught herein to the stained surface. Afterwards, the compositions are optionally but desirably wiped, scrubbed or otherwise physically contacted with the hard surface, and further optionally, may be subsequently rinsed from such a cleaned and disinfected hard surface.

The inventive compositions are particularly useful as ready to use aqueous cleaning and disinfecting compositions which are effective in the eradication of, or in providing a reduction in the amount of gram positive or gram negative such as *Staphylococcus aureus, Salmonella choleraesuis* and *Pseudomonas aeruginosa.*

It is to be understood that the foregoing are provided by way of example, and not by way of limitation and it is expected that the compositions will be useful for eradication of still further gram positive or gram negative type organisms although not specifically elucidated herein.

The hard surface cleaning and disinfecting composition provided according to the invention is conveniently provided as a ready-to-use product in a manually operated spray dispensing container. Such a typical container is generally made of synthetic polymer plastic material such as polyethylene, polypropylene, polyvinyl chloride or the like and includes spray nozzle, a dip tube and associated pump dispensing parts and is thus ideally suited for use in a consumer "spray and wipe" application. In such an application, the consumer generally applies an effective amount of the cleaning composition using the pump and, within a short time thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposit after which it may then be wiped off, rinsed off, or otherwise removed. For particularly heavy deposits of such undesired stains, multiple applications may also be used.

In a yet further embodiment, the compositions according to the invention may also be formulated so that they are be provided as an "aerosol" type product which is discharged from a pressurized aerosol container. If the inventive compositions are used in an aerosol type product, it is preferred that corrosion resistant aerosol containers such as coated or lined aerosol containers be used. Such are preferred as they are known to be resistant to the effects of acidic formulations. Known art propellants such as liquid propellants as well as propellants of the non-liquid form, i.e., pressurized gases, including carbon dioxide, air, nitrogen, hydrocarbons as well as others may be used. Also, while satisfactory for use, fluorocarbons may be used as a propellant but for environmental and regulatory reasons their use is preferably avoided. In this embodiment, the composition is dispensed by activating the release nozzle of said aerosol type container onto the stain and/or stain area and, in accordance with a manner as above-described a stain is treated and removed.

Whereas compositions of the present invention are intended as a ready to use product and is not specifically intended to be diluted into a further volume of water, nothing in this specification shall be understood as to limit the use of said compositions with a further amount of water to form a cleaning and disinfecting solution. In such a proposed diluted cleaning solution, the greater the proportion of water added to form said cleaning and disinfecting dilution, the greater may be the reduction of the rate and/or efficacy of the thus formed cleaning and disinfecting solution in the treatment of a hard surface. Thus, an undesirable reduction in disinfectant efficacy may result and accordingly, longer residence times on the surface to be treated may be required in order to satisfactorily loosen stains and soils and provide a sufficient disinfecting effect. Alternatively, the usage of greater amounts and/or multiple treatments with such a disinfecting solution may be necessitated. Conversely, nothing in the specification shall be also understood to limit the forming of a "super-concentrated" cleaning and disinfecting composition based upon the composition described above. Such a super-concentrated composition is essentially the same as the compositions described above except in that they include a lesser amount of water.

EXAMPLES

Exemplary formulations illustrating certain preferred embodiments of the inventive compositions which are described in more detail in Table 1 were formulated generally in accordance with the following protocol.

Into a suitably sized vessel, a measured amount of water was provided after which the constituents were added in the following sequence: surfactants, alcohol and glycol ethers, hydrogen peroxide, acid, and, lastly the coloring and fragrance constituents. All of the constituents were supplied at room temperature, and mixing of the constituents was achieved by the use of a mechanical stirrer with a small diameter propeller at the end of its rotating shaft. Mixing, which generally lasted from 5 minutes to 120 minutes was maintained until the particular exemplary formulation appeared to be homogeneous. The exemplary compositions were readily pourable, and retained well mixed characteristics (i.e., stable mixtures) upon standing for extend periods, even in excess of 120 days.

It is to be noted that the constituents may be added in any order, but it is preferred that water be the initial constituent provided to a mixing vessel or apparatus as it is the major constituent and addition of the further constituents thereto is convenient.

The exact compositions of the example formulations are listed on Table 1, below wherein the individual constituents were used as supplied from its source. Deionized water was added in quantum sufficient ("q.s.") to provide 100%wt. of the example formulations.

TABLE 1

| | Ex. 1 | Ex. 2* |
|---|---|---|
| NEODOL 23-6.5 | 2.5 | 2.5 |
| NEODOL 91-8 | 4.0 | 4.0 |
| DOWANOL DPnB | 5.0 | 5.0 |
| ethanol (95% vol.) | 5.0 | 5.0 |
| citric acid | 2.87 | 2.87 |
| hydrogen peroxide (50%) | 3.0 | 3.0 |
| fragrance | 0.20 | 0.20 |
| deionized water | 77.43 | 77.43 |

TABLE 1-continued

| | Ex. 3 | Ex. 4 | Ex. 5 | Ex. 6 | Ex. 7 |
|---|---|---|---|---|---|
| AMMONYX LO | 1.0 | 1.0 | 1.0 | 1.0 | 1.0 |
| SLS (30%) | — | — | — | — | — |
| MACKAM 151L | — | — | — | — | — |
| DOWANOL DB | 5.0 | 5.0 | 5.0 | 5.0 | 5.0 |
| ethanol (95%) | 5.0 | 5.0 | 5.0 | 5.0 | 5.0 |
| sulfamic acid | 1.0 | — | — | — | — |
| malic acid | — | 3.0 | — | — | — |
| glutaric acid | — | — | — | — | 3.0 |
| $H_3PO_4$ (85%) | — | — | — | 1.0 | — |
| Glycolic acid | — | — | 3.0 | — | — |
| hydrogen peroxide (50%) | 12.0 | 12.0 | 12.0 | 12.0 | 12.0 |
| fragrance | 0.2 | 0.2 | 0.2 | 0.2 | 0.2 |
| d.i. water | q.s. | q.s. | q.s. | q.s. | q.s. |
| pH | 1.41 | 2.28 | 2.39 | 1.82 | 2.87 |

| | Ex. 8 | Ex. 9 | Ex. 10 | Ex. 11 | Ex. 12 |
|---|---|---|---|---|---|
| AMMONYX LO | — | — | — | — | — |
| SLS (30%) | 1.0 | 1.0 | 1.0 | 1.0 | 1.0 |
| MACKAM 151L | — | — | — | — | — |
| DOWANOL DB | 5.0 | 5.0 | 5.0 | 5.0 | 5.0 |
| ethanol (95%) | 5.0 | 5.0 | 5.0 | 5.0 | 5.0 |
| sulfamic acid | 1.0 | — | — | — | — |
| malic acid | — | 3.0 | — | — | — |
| glutaric acid | — | — | — | — | 3.0 |
| $H_3PO_4$ (85%) | — | — | — | 1.0 | — |
| glycolic acid | — | — | 3.0 | — | — |
| hydrogen peroxide (50%) | 12.0 | 12.0 | 12.0 | 12.0 | 12.0 |
| fragrance | 0.2 | 0.2 | 0.2 | 0.2 | 0.2 |
| d.i. water | q.s. | q.s. | q.s. | q.s. | q.s. |
| pH | 1.07 | 1.91 | 2.00 | 1.61 | 2.40 |

| | Ex. 13 | Ex. 14 | Ex. 15 | Ex. 16 | Ex. 17 |
|---|---|---|---|---|---|
| AMMONYX LO | — | — | — | — | — |
| SLS (30%) | — | — | — | — | — |
| MACKAM 151L | 1.0 | 1.0 | 1.0 | 1.0 | 1.0 |
| DOWANOL DB | 5.0 | 5.0 | 5.0 | 5.0 | 5.0 |
| ethanol (95%) | 5.0 | 5.0 | 5.0 | 5.0 | 5.0 |
| sulfamic acid | 1.0 | — | — | — | — |
| malic acid | — | 3.0 | — | — | — |
| glutaric acid | — | — | 3.0 | — | — |
| $H_3PO_4$ (85%) | — | — | — | 1.0 | — |
| glycolic acid | — | — | — | — | 3.0 |
| hydrogen peroxide (50%) | 12.0 | 12.0 | 12.0 | 12.0 | 12.0 |
| fragrance | 0.2 | 0.2 | 0.2 | 0.2 | 0.2 |
| d.i. water | q.s. | q.s. | q.s. | q.s. | q.s. |
| pH | 2.79 | 2.17 | 2.79 | 1.64 | 2.25 |

| | Ex. 18 | Ex. 19 | Ex. 20 |
|---|---|---|---|
| AMMONYX LO | 1.0 | — | — |
| SLS (30%) | — | 1.0 | — |
| MACKAM 151L | — | — | 1.0 |
| DOWANOL DB | 5.0 | 5.0 | 5.0 |
| ethanol (95%) | 5.0 | 5.0 | 5.0 |
| sulfamic acid | 1.0 | — | — |
| malic acid | — | — | — |
| glycolic acid | — | 3.0 | |
| $H_3PO_4$ (85%) | — | — | 1.0 |
| Glycolic acid | — | — | |
| hydrogen peroxide (50%) | 8.0 | 8.0 | 8.0 |
| fragrance | 0.2 | 0.2 | 0.2 |
| d.i. water | q.s. | q.s. | q.s. |
| pH | 1.25 | 2.06 | 1.78 |

*the formulation of Ex. 1 is the same that of Ex. 2, but from a different batch

The identity of the particular constituents recited in Table 1 is disclosed in particular detail in Table 2.

TABLE 2

| | |
|---|---|
| NEODOL 23-6.5 | nonionic alcohol $C_{12}$–$C_{15}$ ethoxylate (6.5 mol EO) (100% wt. actives) |
| NEODOL 91-8 | nonionic alcohol $C_9$–$C_{11}$ethoxylate (8 mol EO) (100% wt. actives) |
| AMMONYX LO | (30% wt. active) ex. Stepan Co., Northfield IL |
| SLS (30%) | sodium lauryl sulfate (30% wt. active) ex. Witco Corp., Dublin OH |
| MACKAM 151L | lauraminopropionic acid (40% wt. active) (amphoteric surfactant) ex. McIntyre Group Ltd., University Park, IL |
| DOWANOL DPnB | dipropylene glycol butyl ether (100% wt. actives) ex. Dow Chemical Co., Midland MI |
| DOWANOL DB | (100% wt. actives) |
| ethanol (95% vol.) | ethanol (95% vol. active) |
| citric acid | anhydrous citric acid |
| sulfamic acid | anhydrous sulfamic acid (100% wt. active) ex. American International Chemical, Natick, MA |
| malic acid | anhydrous malic acid (100% wt. active) ex. Bartek Ingredients Inc., Ontario, Canada |
| glycolic acid | glycolic acid (70% wt. active) ex. DuPont Specialty Chemicals, Wilmington, DE |
| glutaric acid | anhydrous glutaric acid (100% wt. active) ex: ICN Biomedicals, Aurora, OH |
| $H_3PO_4$ | phosphoric acid (85% wt. active) ex. FMC Corp., |
| hydrogen peroxide (50%) | aqueous hydrogen peroxide (50% wt. actives) |
| fragrance | proprietary composition |
| d.i. water | deionized water |

Evaluation of Antimicrobial Efficacy:

The formulations of Ex. 1 and Ex.2 described in more detail on Table 1 above were evaluated for their antimicrobial efficacy against *Staphylococcus aureus* (gram-positive type pathogenic bacteria) (ATCC 6538), *Salmonella choleraesuis* (gram-negative type pathogenic bacteria) (ATCC 10708), and *Pseudomonas aeruginosa* (ATCC 15442). Similarly the formulations according to Ex. 3 to Ex. 20, as described in Table 1 above, were evaluated for their antimicrobial efficacy against *Pseudomonas aeruginosa* (ATCC 15442).

The testing was performed in accordance with the protocols outlined in "Use-Dilution Method", Protocols 955.14, 955.15 and 964.02 described in Chapter 6 of "Official Methods of Analysis", 16$^{th}$ Edition, of the Association of Official Analytical Chemists; "Germicidal and Detergent Sanitizing Action of Disinfectants", 960.09 described in Chapter 6 of "Official Methods of Analysis", 15$^{th}$ Edition, of the Association of Official Analytical Chemists; or American Society for Testing and Materials (ASTM) E 1054-91 the contents of which are herein incorporated by reference. This test is also commonly referred to as the "AOAC Use-Dilution Test Method".

As is appreciated by the skilled practitioner in the art, the results of the AOAC Use-Dilution Test Method indicate the number of test substrates wherein the tested organism remains viable after contact for 10 minutes with a test disinfecting composition/total number of tested substrates (cylinders) evaluated in accordance with the AOAC Use-Dilution Test. Thus, a result of "0/60" indicates that of 60 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition.

Results of the antimicrobial testing are indicated on Table 3. The reported results indicate the number of test cylinders with live test organisms/number of test cylinders tested for each example formulation and organism tested.

TABLE 3

| Example Formulation | *Staphylococcus aureus* | *Salmonella choleraesuis* | *Pseudomonas aeruginosa* |
|---|---|---|---|
| Ex. 1 | 0/60 | 0/60 | 0/60 |
| Ex. 2 | 0/60 | 0/60 | 0/60 |
| Ex. 3 | — | — | 0/10 |
| Ex. 4 | — | — | 0/10 |
| Ex. 5 | — | — | 0/10 |
| Ex. 6 | — | — | 0/10 |
| Ex. 7 | — | — | 0/10 |
| Ex. 8 | — | — | 0/10 |
| Ex. 9 | — | — | 0/10 |
| Ex. 10 | — | — | 0/10 |
| Ex. 11 | — | — | 0/10 |
| Ex. 12 | — | — | 0/10 |
| Ex. 13 | — | — | 0/10 |
| Ex. 14 | — | — | 0/10 |
| Ex. 15 | — | — | 0/10 |
| Ex. 16 | — | — | 0/10 |
| Ex. 17 | — | — | 0/10 |
| Ex. 18 | — | — | 0/10 |
| Ex. 19 | — | — | 0/10 |
| Ex. 20 | — | — | 0/10 |

From the results reported on Table 3, it is seen that the formulations according to Ex. 1 and Ex.2 are appropriately categorized as a "hospital strength" type disinfecting composition as they exhibit antimicrobial efficacy against all three of the bacteria *Staphylococcus aureus, Salmonella choleraesuis*, and *Pseudomonas aeruginosa* in accordance with the AOAC Use-dilution Test method outlined above. Similarly, the formulations according to Ex. 3 through Ex. 20 exhibited good antimicrobial efficacy against *Pseudomonas aeruginosa* according to the same test method.

From the foregoing, it is to be understood that the compositions according to the invention provide excellent disinfecting benefits to hard surfaces, including hard surfaces. Such compositions in accordance with the present inventive teaching are particularly advantageously used against known bacteria commonly found in bathroom, kitchen and especially in hospital and health care environments. Still further, the efficacy of these compositions is believed effective against the polio virus as well. Such advantages clearly illustrate the superior characteristics of the compositions which, notwithstanding the relatively low content of volatile organic materials, surprisingly provide excellent antimicrobial benefits.

While the invention is susceptible of various modifications and alternative forms, it is to be understood that specific embodiments thereof have been shown by way of examples which however are not intended to limit the invention to the particular forms disclosed; on the contrary the intention is to cover all modifications, equivalents and alternatives falling within the scope and spirit of the invention as expressed in the appended claims.

What is claimed is:

1. A ready to use aqueous cleaning and disinfecting composition which includes the following constituents by weight:

0.1–20%wt. of a C1–C6 monohydric alcohol;

1.0–10%wt. of a glycol ether, or butoxypropanol or propoxypropanol;

0.1–12%wt. of a detersive surfactant selected from the group consisting of: anionic, cationic, nonionic and amphoteric surfactants;

0.1–10%wt. of hydrogen peroxide;

0.1–7%wt. of an acid;

to 100%wt. water;

wherein the said composition is at an acidic pH and which may optionally include minor amounts, to about 2.5%wt. of one or more optional constituents.

2. The ready-to-use aqueous cleaning and disinfecting composition according to claim 1 which further comprises: 0–2.5%wt. of one or more optional constituents selected from the group consisting of: foaming agents, foam stabilizing agents, fragrances, fragrance solubilizers, coloring agents, pH adjusting agents, pH buffering agents, thickening agents and gelling agents.

3. The ready-to-use aqueous cleaning and disinfecting composition according to claim 1 which comprises 1–12%wt. of a $C_1$–$C_6$monohydric alcohol.

4. The ready-to-use aqueous cleaning and disinfecting composition according to claim 3 which comprises 3–7%wt. of a $C_1$–$C_6$ monohydric alcohol.

5. The ready-to-use aqueous cleaning and disinfecting composition according to claim 1 which comprises a glycol ether selected from the group consisting of: ethylene glycol monobutyl ether, diethylene glycol monobutyl ether, mono-, di- or tri-propylene glycol butyl ethers.

6. The ready-to-use aqueous cleaning and disinfecting composition according to claim 1 which comprises butoxypropanol or propoxypropanol.

7. The ready-to-use aqueous cleaning and disinfecting composition according to claim 1 which comprises 0.1–12%wt. of a nonionic surfactant based on alkoxylated linear primary alcohols, alkoxylated linear secondary alcohols, or aloxylated alkyl phenols.

8. The ready-to-use aqueous cleaning and disinfecting composition according to claim 1 which comprises 0.1–12%wt. of an anionic surfactant.

9. The ready-to-use aqueous cleaning and disinfecting composition according to claim 1 which comprises 0.1–12%wt. of an cationic surfactant.

10. The ready-to-use aqueous cleaning and disinfecting composition according to claim 1 which comprises 0.1–12%wt. of an amphoteric surfactant.

11. The ready-to-use aqueous cleaning and disinfecting composition according to claim 1 which comprises 0.1–12%wt. of an nonionic surfactant.

12. The ready-to-use aqueous cleaning and disinfecting composition according to claim 1 wherein the said composition is at pH of about 4 and less.

13. The ready-to-use aqueous cleaning and disinfecting composition according to claim 12 wherein the said composition is at pH of about 3.5 and less.

14. A ready-to-use aqueous cleaning and disinfecting composition according to claim 1 which is effective against gram-positive type pathogenic bacteria.

15. A ready-to-use aqueous cleaning and disinfecting composition according to claim 1 which is effective against gram-negative type pathogenic bacteria.

16. A ready-to-use aqueous cleaning and disinfecting composition according to claim 1 which is effective against at least one bacteria selected from the group consisting of: *Staphylococcus aureus, Salmonella choleraesuis*, or *Pseudomonas aeruginosa.*

17. A ready-to-use aqueous cleaning and disinfecting composition according to claim 16 which is effective against at least two bacteria selected from the group consisting of: *Staphylococcus aureus, Salmonella choleraesuis*, or *Pseudomonas aeruginosa.*

18. A ready-to-use aqueous cleaning and disinfecting composition according to claim 16 which is effective against at all three bacteria: *Staphylococcus aureus, Salmonella choleraesuis*, or *Pseudomonas aeruginosa.*

19. A process for the disinfection of hard surfaces wherein the presence of gram-negative type pathogenic bacteria is suspected which comprises the process step of:

applying a germicidally effective amount of the composition according to claim 1.

20. A process for the disinfection of hard surfaces wherein the presence of gram-positive type pathogenic bacteria is suspected which comprises the process step of:

applying a germicidally effective amount of the composition according to claim 1.

21. A process for the disinfection of hard surfaces wherein the presence of one or more bacteria selected from the group consisting of: *Staphylococcus aureus, Salmonella choleraesuis*, or *Pseudomonas aeruginosa* is suspected which comprises the process step of:

applying a germicidally effective amount of the composition according to claim 1.

* * * * *